United States Patent
Liu et al.

(10) Patent No.: US 9,914,795 B2
(45) Date of Patent: Mar. 13, 2018

(54) POLYMERS POLYMERIZED FROM AT LEAST FOUR MONOMERS, AND COMPOSITIONS AND USES THEREOF

(71) Applicant: ISP INVESTMENTS INC., Wilmington, DE (US)

(72) Inventors: Xuejun Liu, Whippany, NJ (US); Osama M. Musa, Kinnelon, NJ (US)

(73) Assignee: ISP INVESTMENTS LLC, Wilmington, DE (US)

(*) Notice: Subject to any disclaimer, the term of this patent is extended or adjusted under 35 U.S.C. 154(b) by 19 days.

(21) Appl. No.: 14/759,813

(22) PCT Filed: Jan. 9, 2014

(86) PCT No.: PCT/US2014/010782
§ 371 (c)(1),
(2) Date: Jul. 8, 2015

(87) PCT Pub. No.: WO2014/110203
PCT Pub. Date: Jul. 17, 2014

(65) Prior Publication Data
US 2015/0353663 A1 Dec. 10, 2015

Related U.S. Application Data

(60) Provisional application No. 61/750,582, filed on Jan. 9, 2013.

(51) Int. Cl.
| | | |
|---|---|---|
| *C08F 220/10* | (2006.01) |
| *A61K 8/81* | (2006.01) |
| *A61Q 17/04* | (2006.01) |
| *C08K 5/132* | (2006.01) |
| *C09D 11/107* | (2014.01) |
| *C09D 133/10* | (2006.01) |
| *C09J 133/10* | (2006.01) |
| *D21H 17/37* | (2006.01) |
| *C08F 226/08* | (2006.01) |
| *C08F 220/18* | (2006.01) |

(52) U.S. Cl.
CPC .......... *C08F 220/10* (2013.01); *A61K 8/8182* (2013.01); *A61Q 17/04* (2013.01); *C08F 220/18* (2013.01); *C08F 226/08* (2013.01); *C08K 5/132* (2013.01); *C09D 11/107* (2013.01); *C09D 133/10* (2013.01); *C09J 133/10* (2013.01); *D21H 17/37* (2013.01)

(58) Field of Classification Search
CPC .... C08F 226/08; C08F 220/18; C08F 220/10; C08F 2220/1825; C08F 220/06; C08F 2220/1875; A61Q 17/04; D21H 7/37; C09D 11/107; C09D 133/10; A61K 8/8182; C08K 5/132; C09J 133/10
See application file for complete search history.

(56) References Cited

U.S. PATENT DOCUMENTS

| | | | |
|---|---|---|---|
| 3,692,893 A | 9/1972 | Palmer | |
| 5,997,855 A | 12/1999 | Liu | |
| 2002/0076390 A1* | 6/2002 | Kantner | A61K 8/8147 424/70.16 |
| 2004/0266953 A1 | 12/2004 | Charmot et al. | |
| 2007/0299206 A1 | 12/2007 | Cooper et al. | |
| 2008/0089853 A1* | 4/2008 | Nguyen-Kim | A61K 8/817 424/61 |
| 2008/0207767 A1 | 5/2008 | Dobos et al. | |
| 2010/0041846 A1 | 2/2010 | Hood | |
| 2010/0069566 A1* | 3/2010 | Mae | C08F 265/04 524/560 |
| 2011/0159300 A1 | 6/2011 | Rodowski et al. | |
| 2012/0130036 A1 | 5/2012 | Ulmer et al. | |

FOREIGN PATENT DOCUMENTS

| | | | | |
|---|---|---|---|---|
| WO | WO 2011000688 A1 * | 1/2011 | ............. | C09K 5/063 |
| WO | WO 2012/051153 A2 | 4/2012 | | |
| WO | WO 2012/148533 A1 | 11/2012 | | |

OTHER PUBLICATIONS

International Search Report, PCT/US2014/010782 published on Jul. 17, 2014.

* cited by examiner

*Primary Examiner* — Anoop K Singh
*Assistant Examiner* — Doan T Phan
(74) *Attorney, Agent, or Firm* — Thompson Hine LLP; William J. Davis

(57) ABSTRACT

Described herein is a class of non-homopolymers polymerized from at least: (A) 10-22 mole percent of at least one N-vinyl lactam, (B) 30-35 mole percent of at least one monomer selected from the group consisting of acrylic acid, methacrylic acid, and combinations thereof, (C) 40-52 mole percent of at least one (meth)acrylate of a straight- or branched-chain alkyl alcohol, and (D) 5-20 mole percent of at least one (meth)acrylate of a saturated or unsaturated cyclic alcohol having 6 to 20 carbon atoms. In one embodiment, the non-homopolymers exhibit solubility in the lower molecular weight alcohols. The non-homopolymers may be used in personal care or performance chemicals compositions. In one embodiment, the polymers are used in various personal care formulations, such as used for skin, sun, hair, and preservatives.

18 Claims, 1 Drawing Sheet

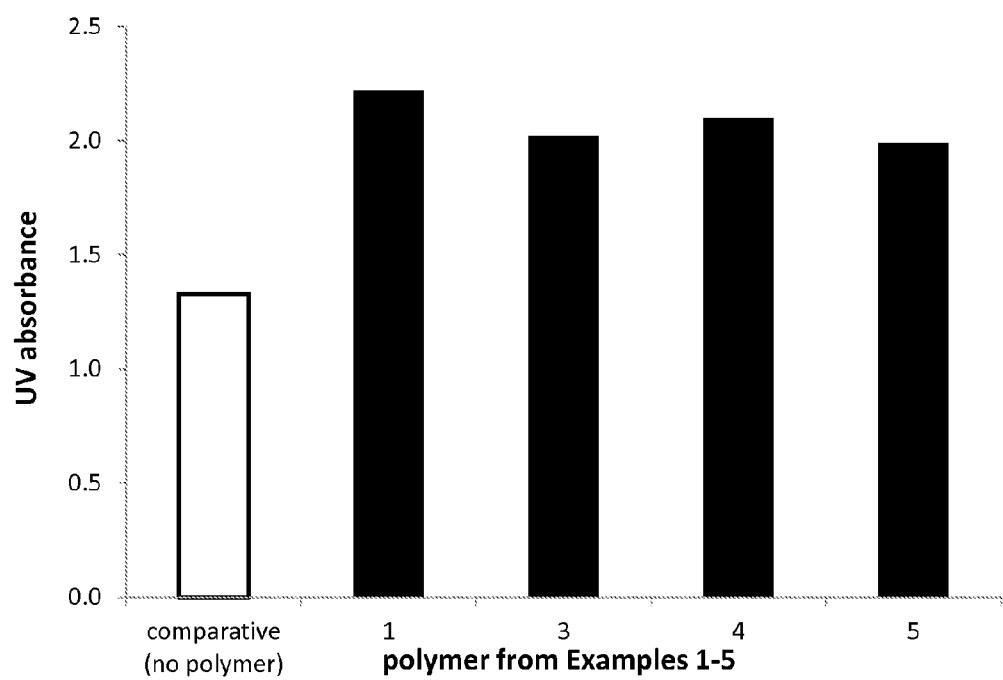

US 9,914,795 B2

POLYMERS POLYMERIZED FROM AT LEAST FOUR MONOMERS, AND COMPOSITIONS AND USES THEREOF

BACKGROUND

Field of the Invention

The invention is directed to non-homopolymers that are polymerized from at least four polymerizable monomers. In one embodiment, the polymers are soluble in at least one lower molecular weight alcohol such as methanol, ethanol, 1-propanol, or 2-propanol.

Description of Related Art

Formulation scientists often face multiple challenges when developing new or reformulating existing products. Many times, products must attain target attributes that can only be achieved by one or more polymers, properties like UV absorption, adhesion, shine, smoothness, texture, binding, and/or water solubility/insolubility profile. For optimal performance, the polymer(s) must be soluble in an amenable solvent system, either during product formulation or end use. Due to its low toxicity, cost, and boiling point, ethanol and other low molecular weight alcohols are a solvent of choice for many products, especially cosmetics for use on the skin or hair.

Unfortunately, there is a limited selection of polymers soluble in lower molecular weight alcohols that also exhibit advanced functionality required for next-generation products. For example, while poly(vinyl alcohol) demonstrates excellent film strength, it flakes easily. To overcome these solubility and/or property deficiencies, polymers are often engineered as non-homopolymers to exploit the benefits of two or more monomer units. However, the polymer scientist must balance sometimes competing constraints between performance and solubility. Hence, needed are polymers that are soluble in the lower molecular weight alcohols which also satisfy the demands of product performance.

The related art teaches various polymers used in the cosmetic arts and their uses. Representative U.S. patent applications include 2002/0076390, 2002/0146515, 2004/0132863, 2005/0065252, 2005/0222322, 2005/0265949, 2007/0086959, 2010/0080763, and U.S. Pat. Nos. 4,486,577; 4,508,884; 5,662,892; 5,912,294; 6,126,929; 6,686,413; 7,048,916; 7,122,175; and 7,144,928. These publications teach polymers of differing compositions for use in applications ranging from cosmetics (e.g., hair, skin, nails) to floor polish and contact lens.

An acrylic resin is taught in U.S. patent application 2005/0065252 that is derived from a $C_1$ to $C_{14}$ (meth)acrylate, a 5- or more-member heterocyclic monomer, and a monomer having at least two olefinic double bonds. Composition [7] in this application is a polymer derived from a $C_1$ to $C_{14}$ (meth)acrylate, a 5- or more-member heterocyclic monomer, an alicyclic monomer, and a monomer containing at least one polar functional group such as a hydroxyl group. However, given the broad range in stated monomer levels, there is no indication that polymers of the '252 patent application should be ethanol soluble.

Personal care polymers are the subject of U.S. patent application 2002/0076390. The polymers are derived from 10%-85% (w/w) hydrophobic first monomer that is a (meth)acrylate of a $C_4$ to $C_{18}$ alkyl alcohol, 10%-70% (w/w) of a hydrophobic second monomer that is (meth)acrylate ester of a cyclic alcohol containing 6 to 20 carbon atoms, and up to 20% (w/w) of an optional hydrophilic third monomer, such as (meth)acrylamide, 2-ethoxyethyl(meth)acrylate or N-vinyl-2-pyrrolidone. The applications states, "The total amount of hydrophilic monomer preferably does not exceed about 20%, more preferably about 10% of the total weight of all monomers, such that excessive hydrophilicity is avoided." As a result of this composition, the application states the glass transition temperature ($T_g$) of the polymers is preferably less than 35° C. Example polymers in Table 1 of the '390 application have a $T_g$ of 15° C. or less, which means they exhibit rubber-like properties at room temperature, and may be too soft and/or tacky for many applications.

Also related is U.S. Pat. No. 7,122,175, which provides a reshapable hair styling composition comprising a (meth)acrylate ester of a $C_4$ to $C_{18}$ alkyl alcohol, a (meth)acrylate ester of a cyclic alcohol, at least one hydrophilic monomer, and, optionally, other monomer units. The '175 patent teaches broad ranges for the prescribed named monomer units. The synthesis methods disclosed in this patent include emulsion polymerization in water with dodecyl benzene sulfonate, solution polymerization in methylethyl ketone followed by inversion in water, and suspension polymerization in water. Additionally, the polymer of Example 1 is taught as a hair styling composition in water. However, the '175 patent does not disclose the existence of alcohol-soluble polymers, let alone enable one skilled in the art how to attain them. Furthermore, the polymers that are taught possess low glass transition temperatures, about –100° C. to about 15° C., which can render them sticky and tacky at room temperature, and which realistically limits their usefulness in the cosmetic arts like skin, sun, and hair care products.

Despite the body of related work in polymer chemistry, there still exists a commercial and industrial need for polymers that are soluble in lower molecular weight alcohols, especially ethanol. Of particular value are alcohol-soluble polymers having a glass transition temperature greater than about 40° C. to enable their use in the cosmetic, adhesive, inks, and coatings arts.

SUMMARY

A family of polymers has been discovered that are polymerized from at least: (A) at least one N-vinyl lactam or N-vinyl amide, such as N-vinyl-2-pyrrolidone, N-vinyl-2-caprolactam or N-vinyl formamide, (B) at least one (meth)acrylic acid, (C) at least one (meth)acrylate of a straight or branched alkyl alcohol, and (D) at least one (meth)acrylate of a $C_6$ to $C_{20}$ cyclic alcohol. In particular embodiments the polymers are used in personal care compositions such as sun care, skin care, and hair care products, and in adhesives, coatings, inks, and inks. In various embodiments, the non-homopolymers exhibit solubility of at least about 1% (w/w) in lower molecular weight alcohols, such as ethanol, 1-propanol, 2-propanol, and/or methanol.

BRIEF DESCRIPTION OF THE DRAWING

The FIGURE is a graph of UV absorbance for five compositions produced in accordance with Example 11.

DETAILED DESCRIPTION

Described herein is a class of polymers being polymerized from at least four monomers: (A) at least one N-vinyl lactam or N-vinyl amide, such as N-vinyl-2-pyrrolidone, N-vinyl-2-caprolactam or N-vinyl formamide, (B) at least one (meth)acrylic acid, (C) at least one (meth)acrylate of a straight or branched alkyl alcohol, and (D) at least one (meth)acrylate of a $C_6$ to $C_{20}$ cyclic alcohol. By selection of each monomer amount, polymers of the invention may be soluble in at least one lower molecular weight alcohol, which extends their use into the arts where ethanol-soluble polymers find application. In one embodiment, the polymers find application in personal care for sun care, skin care, or hair care products.

As used herein, the following terms have the meanings set out below:

The term monomer refers to a repeating structural unit of a polymer. A monomer is generally a low molecular weight compound that can form covalent chemical bonds with itself and/or with other monomers, resulting in a polymer.

The term functional analogue refers a compound or a part of a compound wherein one or more hydrogen atoms has been replaced with one or more non-hydrogen groups, for e.g., alkyl, alkoxy, cycloalkyl, alkenyl, cycloalkenyl, alkynyl, and/or aryl groups. Alkyl, alkenyl and/or alkynyl groups include $C_1$-$C_{60}$, more particularly $C_1$-$C_{36}$, and most particularly $C_1$-$C_{18}$ groups. Cycloalkyl groups include cyclopentane, cyclohexane, cycloheptane, and the like. Alkoxy groups include methoxy, ethoxy, n-propoxy, isopropoxy, and the like. Aryl groups include benzenes, naphthalenes (2 rings), anthracenes (3 rings), and the like.

The term polymer refers to a compound comprising repeating structural units (monomers) connected by covalent chemical bonds. The definition of polymer includes oligomers. Polymers may be functionalized, for example, by chemical reaction to modify existing moieties within the polymer (e.g., hydrolysis), by chemical reaction with one or more reactants to covalently attach—one or more moieties to the polymer, by crosslinking utilizing reactive moieties within the polymer or by reacting with multifunctional crosslinking reactants, grafting or end-capping. Non-limiting examples of polymers include homopolymers, copolymers, terpolymers, and non-homopolymers. A polymer may be a random, block, or an alternating polymer, or a polymer with a mixed random, block, and/or alternating structure. Polymers may further be associated with solvent adducts.

The term non-homopolymer refers to any polymer comprising more than one type of repeating structural units (monomers) connected by covalent chemical bonds. Examples of non-homopolymers include copolymers, terpolymers, and non-homopolymers.

The term (meth)acrylate refers to both acrylate and methacrylate.

The term solvent adduct refers to a solvent molecule that is bonded to a compound, such as a polymer, by one or more covalent bonds, ionic bonds, hydrogen bonds, coordination bonds, and/or Van der Waals forces of attraction.

The term lower molecular weight alcohols refers to alcohols having from one to four carbon atoms. Examples of lower molecular weight alcohols include: methanol, ethanol, 1-propanol, 2-propanol, allyl alcohol, propargyl alcohol, 2-aminoethanol, ethylene glycol, methyl propargyl alcohol, 1-butyn-4-ol, 2-butyn-1-ol, 2-buten-1-ol, 2-butanol, 2-methyl-2-propanol, and tert-butanol. In various embodiments of the invention, the lower molecular weight alcohol may be methanol, ethanol, 1-propanol, 2-propanol, or tert-butanol, or combinations thereof.

The phrase alcohol-soluble non-homopolymer refers to a non-homopolymer that dissolves (perhaps after initial heating, shaking, or stirring) in an amount of about 1% by weight or more at 25° C. in at least one lower molecular weight alcohol to form a transparent or translucent solution.

The terms ultraviolet and UV mean electromagnetic radiation, especially solar electromagnetic radiation, with a wavelength from about 100 nm to about 400 nm, and includes the UV-A, UV-B, and UV-C subclassifications of such radiation.

The term UV-A means ultraviolet electromagnetic radiation with a wavelength from about 320 nm to about 400 nm, and includes UV-A1 (from about 340 nm to about 400 nm) and UV-A2 (from about 320 nm to about 340 nm).

The term UV-B means ultraviolet electromagnetic radiation with a wavelength from about 290 nm to about 320 nm.

The term UV-C means ultraviolet electromagnetic radiation with a wavelength from about 200 nm to about 290 nm.

The term UV absorber means any entity that absorbs, scatters, and/or reflects UV radiation.

The terms personal care composition and cosmetics refer to compositions that are applied anywhere to or on the body of a mammal, such as the human body. Personal care compositions and cosmetics include illustrative non-limiting compositions as skin, sun, oil, hair, and preservative compositions, including those to alter the color, condition, or appearance of the skin or hair. Potential personal care compositions include, but are not limited to, polymers for increased flexibility in styling, durable styling, increased humidity resistance for hair, skin, and color cosmetics, sun care water-proof/resistance, wear-resistance, and thermal protecting/enhancing compositions.

The term pharmaceutical composition refers to any composition finding utility on or in man or animal that comprises one or more active ingredients. This definition includes those compositions sold with and without prescription, branded and unbranded products, as well as those compositions sold into homeopathy markets.

The term performance chemicals composition refers to compositions that are not personal care compositions, cosmetics, or pharmaceutical compositions. Non-limiting examples of performance chemicals compositions include: adhesives; agricultural, biocides, coatings, electronics, household-industrial-institutional (HI&I), inks, membranes, metal fluids, oilfield, paper, paints, plastics, printing, plasters, and wood-care compositions.

All percentages, ratio, and proportions used herein are based on a weight basis unless otherwise specified.

The polymers embraced by the invention include those that demonstrate solubility in at least one lower molecular weight alcohol, and in particular, may be soluble in ethanol.

The polymers are polymerized from at least: (A) 10-22 mole percent of at least one N-vinyl lactam, (B) 30-35 mole percent of at least one (meth)acrylic acid, (C) 40-52 mole percent of at least one (meth)acrylate of a straight or branched alkyl alcohol, and (D) 5-12 mole percent of at least one (meth)acrylate of a $C_6$ to $C_{20}$ cyclic alcohol. The polymers contain higher levels of hydrophilic monomers than taught in U.S. Pat. No. 7,122,175.

Examples of N-vinyl lactams include N-vinyl-2-pyrrolidone, N-vinyl-2-piperidone and N-vinyl-2-caprolactam. The various blended combinations of these N-vinyl lactams may be used.

Examples of (meth)acrylic acids that may be used include acrylic acid and methacrylic acid. Blends of these monomers also may be employed in the invention.

Particular (meth)acrylates of a straight or branched alkyl alcohol include isobutyl acrylate (IBA), isobutyl methacrylate (IBMA), 2-ethylhexyl acrylate (EHA), and 2-ethylhexyl methacrylate (EHMA). Examples of (meth)acrylates of a $C_6$ to $C_{20}$ cyclic alcohols include cyclohexyl(meth)acrylate, cycloheptyl(meth)acrylate, isobornyl methacrylate, isobornyl acrylate, and combinations thereof. In various embodiments the (meth)acrylates of a $C_6$ to $C_{20}$ cyclic alcohols may be isobornyl acrylate, isobornyl methacrylate, or combinations thereof.

The inventors have discovered that the polymers may display a glass transition temperature ($T_g$) higher than known in the related art. Whereas polymers of U.S. patent application 2002/0076390 and U.S. Pat. No. 7,122,175 are characterized by low glass transition temperatures from about −100° C. to about 15° C., polymers of the invention may have a glass transition temperature greater than 40° C., more particularly may be greater than 70° C., and yet more particularly may be greater than 100° C. Glass transition is a well-known property that can be measured by analytical test equipment designed for its measurement, such as the various types of differential scanning calorimeters (DSC). The Examples that follow illustrate a few DSC measurements for polymers of the invention.

One skilled in the art also may estimate $T_g$ values based on monomer type and amounts using numerical modeling techniques and equations.

Due to the broad invention scope, many different polymers may be synthesized using the methods described above. By way of illustration, particular polymers include the 8 polymers that can be produced (A) when N-vinyl lactam unit is N-vinyl-2-pyrrolidone, (B) the (meth)acrylic acid is acrylic acid or methacrylic acid, (C) the (meth)acrylate of a straight or branched alkyl alcohol is isobutyl methacrylate or isobutyl acrylate, and (D) the (meth)acrylate of a $C_6$ to $C_{20}$ cyclic alcohol is isobornyl methacrylate or isobornyl acrylate. These polymers include:

poly(VP-acrylic acid-isobutyl acrylate-isobornyl acrylate)

poly(VP-acrylic acid-isobutyl methacrylate-isobornyl acrylate)

poly(VP-acrylic acid-isobutyl methacrylate-isobornyl methacrylate)

poly(VP-acrylic acid-isobutyl acrylate-isobornyl methacrylate)

poly(VP-methacrylic acid-isobutyl acrylate-isobornyl acrylate)

poly(VP-methacrylic acid-isobutyl methacrylate-isobornyl acrylate)

poly(VP-methacrylic acid-isobutyl methacrylate-isobornyl methacrylate)

poly(VP-methacrylic acid-isobutyl acrylate-isobornyl methacrylate)

One particular combination of these monomers and the resulting polymer can be represented by the reaction scheme:

wherein the subscripts a, b, c, and d represent molar fractions that add to 100%. Of course, many other monomer combinations can be reacted to synthesize particular polymers within this family. Blends of these polymers also are incorporated by the invention. In this illustration and for each of the examples provided later, the polymer may be a random, block, or alternating polymer.

Other particular polymers are those wherein the (A)N-vinyl lactam monomer is N-vinyl-2-caprolactam. This monomer is more hydrophobic than N-vinyl-2-pyrrolidone, and in order to maintain ethanol solubility of the resulting polymer, it may be necessary to balance the molar amounts of N-vinyl-2-caprolactam and the other more hydrophilic monomer (B) with the hydrophobic monomers (C) and (D).

Other non-limiting examples of non-homopolymers of the invention include:

poly(VCL-acrylic acid-isobutyl acrylate-isobornyl acrylate)

poly(VCL-acrylic acid-isobutyl methacrylate-isobornyl acrylate)

poly(VCL-acrylic acid-isobutyl methacrylate-isobornyl methacrylate)

poly(VCL-acrylic acid-isobutyl acrylate-isobornyl methacrylate)

poly(VCL-methacrylic acid-isobutyl acrylate-isobornyl acrylate)

poly(VCL-methacrylic acid-isobutyl methacrylate-isobornyl acrylate)

poly(VCL-methacrylic acid-isobutyl methacrylate-isobornyl methacrylate)

poly(VCL-methacrylic acid-isobutyl acrylate-isobornyl methacrylate)

The hydrophilic-hydrophobic balance also can be modulated by using a blend of N-vinyl lactams, such as combinations of VP and VCL.

Free radical polymerization methods known to one skilled in the art may be employed to create the polymers described herein. These methods include, but are not limited to: solution polymerization, emulsion polymerization, and precipitation polymerization. Free radical polymerization may be employed when using thermally decomposed polymerization initiators, and is described in "Decomposition Rate of Organic Free Radical Polymerization" by K. W. Dixon (section II in *Polymer Handbook, volume 1, 4$^{th}$ edition*, Wiley-Interscience, 1999), which is incorporated by reference. Another description of the free-radical polymerization process is given in U.S. Pat. No. 2,882,262.

The reactants, comprising the at least four polymerizable monomers, may be charged in portions or charged together into a reactor and stirred at a temperature to facilitate the reaction, being limited only by the decomposition temperature of any reactant. The reaction can be performed with and without added solvent. The addition of an optional inert solvent may be beneficial when a high viscosity of the reacting system limits effective reactive processing (i.e., has a high viscosity).

It is within the scope of this invention to employ any combination of the described polymerizable unit(s) (e.g., N-vinyl lactams, (meth)acrylic acids, (meth)acrylates). It may be advantageous to add the least reactive reactants first, and the more reactive ones later in the preparation. As necessary, additional reactive species can be attached to the polymer.

It may be beneficial and desirable to remove any amount of unreacted reactant and/or side product from the final reaction product using methods that are known in the art, including distillation, inversion precipitation, and chromatography.

The reaction may be carried out for times ranging from 30 seconds to 48 hours or even more, and may depend upon factors that include (1) the reactivity of the reactants, (2) the number of reactive groups, since one or more of the reactants may have more than one reactive group, (3) steric hindrance surrounding any reactive site, (4) the reaction temperature employed, (5) the presence or absence of a solvent, and (6) the use or non-use of an initiator and/or catalyst. With the use of an optional reaction solvent or solvents, it may be particular to remove the solvent(s) after the reaction, e.g., at reduced pressure and/or elevated temperature, and then to add a different solvent conducive to the final formulation.

Typically, the molecular weight of the polymer ranges from about 1,000 Da to about 5,000,000 Da, and more particularly the molecular weight ranges from about 10,000 Da to about 1,000,000 Da. As described later, the molecular weight of a polymerized product may be altered by the addition of an optional chain transfer agent (such as isopropanol or carbon tetrabromide) in the customary amounts to the reaction vessel.

For solution reactions, temperatures may be conveniently controlled by judicious choice of solvents within an appropriate boiling range. Temperatures in this case range from 40° C. to about 140° C., particularly from 50° C. to 120° C., and more particularly from 60° C. to 100° C. Reaction times for solution reaction range from several minutes to 48 hours or more. Higher reaction temperatures and highly reactive reactants will reduce time for conversion to the desired product(s). Reaction times may range between 60 minutes and 12 hours, and more particularly between 120 minutes and 10 hours.

Due to the broad nature of the invention, in general a free radical addition polymerization initiator may be beneficial. However, in some synthesis routes, an initiator is not needed to produce the disclosed polymers.

Free-Radical Polymerization

Compounds capable of initiating the free-radical polymerization include those materials known to function in the prescribed manner, and include the peroxide and azo classes of materials. Exemplary peroxide and azo compounds include, but are not limited to: acetyl peroxide; azobis-(2-amidinopropane)dihydrochloride; azobis-isobutyronitrile (AIBN); 2,2'-azobis-(2-methylbutyronitrile); benzoyl peroxide; di-tert-amyl peroxide; di-tert-butyl diperphthalate; tert-butyl peroxy-2-ethylhexanoate; tert-amyl peroxy-2-ethylhexanoate; tert-butyl hydroperoxide; tert-butyl peroxybenzoate; tert-butyl peroxymaleate; tert-butyl peroxyisobutylrate; tert-butyl peroxyacetate; tert-butyl peroxypivalate; para-chlorobenzoyl peroxide; cumene hydroperoxide; diacetyl peroxide; dicumyl peroxide; didecanoyl peroxide; dilauroyl peroxide; diisopropyl peroxodicarbanate; dioctanoyl peroxide; succinyl peroxide; and bis-(orthotoluoyl) peroxide. Tert-amyl peroxy-2-ethylhexanoate is a particular initiator for a number of the particular compositions described herein.

Also suitable to initiate the free-radical polymerization are initiator mixtures or redox initiator systems, including: ascorbic acid/iron(II) sulfate/sodium peroxodisulfate, tert-butyl hydroperoxide/sodium disulfite, and tert-butyl hydroperoxide/sodium hydroxymethanesulfinate.

A chain transfer agent optionally may be used to control the degree of polymerization of the polymer, and thereby control the molecular weight and molecular weight distribution of the product. As a skilled artisan can appreciate, the chain transfer agent may become part of the polymer.

The chain transfer agent may be of the kind that has a carbon-sulfur covalent bond. The carbon-sulfur covalent bond has usually absorption peak in a wave number region ranging from 500 to 800 $cm^{-1}$ in an infrared absorption spectrum. When the chain transfer agent is incorporated into the polymer, the absorption peak of the product may be changed in comparison to product made without a chain transfer agent.

Exemplary chain transfer agents include, but are not limited to, n-$C_3$-$C_{15}$ alkylmercaptans such as n-propylmercaptan, n-butylmercaptan, n-amylmercaptan, n-hexylmercaptan, n-heptylmercaptan, n-octylmercaptan, n-nonylmercaptan, n-decylmercaptan, and n-dodecylmercaptan; branched alkylmercaptans such as isopropylmercaptan, isobutylmercaptan, s-butylmercaptan, tert-butylmercaptan, cyclohexylmercaptan, tert-hexadecylmercaptan, tert-laurylmercaptan, tert-nonylmercaptan, tert-octylmercaptan, and tert-tetradecylmercaptan, allylmercaptan; aromatic ring-containing mercaptans such as, 3-phenylpropylmercaptan, phenylmercaptan, and mercaptotriphenylmethane. As a skilled artisan understands, the term -mercaptan and -thiol may be used interchangeably to mean C—SH group.

Typical examples of such chain transfer agents also include, but are not limited to, dodecanethiol, butanethiol, isooctyl-3-mercaptopropionate, 2-methyl-5-tert-butyl-thiophenol, carbon tetrachloride, carbon tetrabromide, and the like. Dodecanethiol and carbon tetrabromide are most typically used.

Based on total weight of the monomers to be polymerized, the chain transfer agent may generally be present in an amount from about 0.1% to about 7%, including from about 0.5% to about 6%, and from about 1.0% to about 5%, although it may be present in greater or lesser amounts.

The alcohol-soluble polymers described herein may be used in a variety of compositions that can be broadly categorized as personal care compositions or cosmetic compositions (meaning for use on or in the body of a mammal, especially man) and performance chemicals compositions (meaning they are not personal care compositions). The compositions may contain a lower molecular weight alcohol as part of the formulation (since it will dissolve or help to dissolve the polymer in the composition), and/or may be those compositions that come into contact with an alcohol during use (e.g., films created upon the alcohol wetting of polymer powders). The compositions, however, are not required to comprise an alcohol, but instead by comprise other materials, e.g., liquids, gels, and/or semi-solids, to assist in the delivery and/or performance of the invention's polymers.

Personal Care Compositions

In one embodiment, polymers of the invention are formulated into personal care compositions, including skin lotion, skin crèmes, skin ointments, skin salves, anti-aging crèmes, moisturizers, deodorants, tanning agents, sun blocks, foundations, concealers, eyebrow pencils, eye shadows, eye liners, mascaras, rouges, finishing powders, lipsticks, lip gloss, nail polish, make-up removers, nail polish removers, shampoos, rinse-off conditioners, leave-on conditioners, hair styling gels, hair mousses, hair sprays, styling aides, hair colors, and hair color removers. These compositions can benefit from the hydrophobic-hydrophilic balance that can be designed into these alcohol-soluble polymers.

By modulating the monomer types and ratios, an advantageous use of the inventive polymers is its ability to form hydrophobic films. Such applications typically require some amount of water resistance, transfer resistance, or substantivity to skin, nails or hair. Illustrative cosmetic applications include, e.g., mascara, foundation, rouge, face powder, eyeliner, eye shadow, nail polish, and lipstick, i.e., color cosmetics. Illustrative personal care applications include, e.g., hair care products, insect repellent, skin moisturizer, skin cream, body lotion, body spray, and sunscreen.

When the inventive composition is used in hair care products, such as hair styling, gels, mousses, and the like, the dispersion can provide faster drying. It can be used alone as a hair styling agent or used at low levels in combination with other hair styling resins to improve their humidity resistance. The composition can be long lasting, such as 10 to 24 hours, giving rise to a durable styling effect.

Other uses of the polymers in personal care compositions are provided in research disclosures IPCOM 000128968D, available at http://priorartdatabase.com/IPCOM/000128968, and IPCOM 000109682D, available at http://priorartdatabase.com/IPCOM/000109682, both of which are incorporated herein their entirety by reference.

It may be desirable to partially or fully crosslink the polymers of the invention by including a multifunctional crosslinking agent before, during, or after polymerization of the monomers. Partially or fully crosslinking the polymers may help impart, among other properties, enhanced water-resistance and/or rheological properties. The crosslinking agent typically has in the molecule two or more functional groups capable of crosslinking, for example two or more vinyl or allyl moieties, isocyanate moieties, epoxy moieties, metal chelate-based moieties, and aziridine-based moieties. Other related compounds can be identified by one skilled in the art.

Examples of the isocyanate-based compound include tolylene diisocyanate, hexamethylene diisocyanate, isophorone diisocyanate, xylene diisocyanate, hydrogenated xylene diisocyanate, diphenylmethane diisocyanate, hydrogenated diphenylmethane diisocyanate, tetramethylxylene diisocyanate, naphthalene diisocyanate, triphenylmethane triisocyanate, polymethylene polyphenyl isocyanate and the like, and adducts obtained by reacting polyols such as glycerol, trimethylolpropane and the like with the above-mentioned isocyanate compounds, and those obtained by converting the isocyanate compounds into dimers, trimers and the like, are also included.

Examples of the epoxy-based compound include bisphenol A type epoxy resin, ethylene glycol glycidyl ether, polyethylene glycol diglycidyl ether, glycerine glycidyl ether, glycerine triglycidyl ether, 1,6-hexanediol diglycidyl ether, trimethylolpropane triglycidyl ether, diglycidylaniline, N,N,N',N'-tetraglycidyl-m-xylenediamine, 1,3-bis(N,N'-diglycidylaminomethyl)cyclohexane and the like.

Examples of the metal chelate compound include compounds obtained by coordinating acetylacetone or ethyl acetoacetate on poly-valent metals such as aluminum, iron, copper, zinc, tin, titanium, nickel, antimony, magnesium, vanadium, chromium, zirconium and the like.

Examples of the aziridine-based compound include N,N'-diphenylmethane-4,4'-bis(1-aziridine carboxide), N,N'-tolu-ene-2,4-bis(1-aziridine carboxamide), triethylenemelamine, bisisophthaloyl-1-(2-methylaziridine), tri-1-aziridinylphos-phine oxide, N,N'-hexamethylene-1,6-bis(1-aziridine car-boxide), trimethylolpropane-triaziridinyl propionate, tetramethylolmethane-triaziridinyl propionate, and the like.

In addition to a crosslinking agent, adhesives formulated with the inventive polymer may also comprise a weather-resistant agent, tackifier, plasticizer, softening agent, dye/pigment, inorganic filler, and further ingredients.

Personal Care—Sun Care

The personal care composition may be one intended to protect the user from ultraviolet (UV) damage, for example, of the skin and/or hair. Some of the marketed terms these materials are sold by include sun care, all-day care, sun block, and skin care with UV absorbers. In addition to one or more UV absorbers, many of these products contain ethanol which can serve both as a solubilizer and delivery agent (e.g., mist or spray product forms). Polymers of the invention may be formulated into suncare products to impart water-fastness, assist film formation and spreadability, and impart the necessary rheology for product stability and application. Typically, polymer use levels range from 0.5%-5% (weight polymer/total weight of the total suncare formulation), and more particularly ranges from 0.5%-3%, and yet more particularly is about 1% by weight. Blends of polymers may be used.

Polymers of the invention also boost the absorption of UV radiation. As shown in Example 11, the alcohol-soluble polymers of the invention boosted the UV absorbance of a sun care formula by at least 50% compared to a control formula not having polymer. This boost in UV absorbance can allow the formulator to reduce the amount of UV absorber while maintaining total UV absorbance. Alternatively, the original UV absorber use level can be maintained with the inventive polymer(s) to increase the sun protection factor of the sun care product. Combinations of two or more inventive polymers may be used to customizable formulations with regard to sun care properties (e.g., skin feel, spreadability, viscosity) and UV absorbances.

The sun care products that are useful for the present invention contain one or more UV absorbers that may include: octyl salicylate (2-ethylhexyl salicylate, Escalol® 587); pentyl dimethyl PABA; octyl dimethyl PABA (padimate O, Escalol® 507); benzophenone-1; benzophenone-6 (Uvinul® D-49); 2-(2H-benzotriazole-2-yl)-4,6-di-tert-pen-tylphenol (Uvinul® 3028); ethyl-2-cyano-3,3-diphenylacry-late (Uvinul® 3035); homomenthyl salicylate (homosalate); bis-ethylhexyloxyphenol methoxyphenyl triazine (bemo-trizinol, Tinosorb® S); methyl-(1,2,2,6,6-pentamethyl-4-pi-peridyl)-sebacate (Uvinul® 4092H); benzenepropanoic acid, 3,5-bis(1,1-dimethyl-ethyl)-4-hydroxy-, C7-C9 branched alkyl esters (Irganox® 1135); 2-(2H-benzotriaz-ole-2-yl)-4-methylphenol (Uvinul® 3033P); diethylhexyl butamido triazone (iscotrizinol); amyl dimethyl PABA (li-sadimate, glyceryl PABA); 4,6-bis(octylthiomethyl)-o-cresol (Irganox® 1520); CAS number 65447-77-0 (Uvinul® 5062H, Uvinul® 5062GR); red petroleum; ethylhexyl triaz-one (Uvinul® T-150); octocrylene (Escalol® 597); isoamylp-methoxycinnamate (amiloxate, Neo Heliopan® E1000); drometrizole; titanium dioxide; 2,4-di-tert-butyl-6-(5-chloro-2H-benzotriazole-2-yl)-phenol (Uvinul® 3027); 2-hydroxy-4-octyloxybenzophenone (Uvinul® 3008); benzophenone-2 (Uvinul® D-50); diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate (Irganox® 3052); drometrizole trisiloxane (Mexoryl® XL); menthyl anthranilate (meradimate); bis-(1,2,2,6,6-pentamethyl-4-piperidyl)-sebacate; butyl methoxydibenzoylmethane (avobenzone, Escalol® 517); 2-ethoxyethyl p-methoxycinnamate (cinnoxate); benzylidene camphor sulfonic acid (Mexoryl® SL); dimethoxyphenyl-[1-(3,4)]-4,4-dimethyl 1,3-pentanedione; zinc oxide.; N,N'-hexane-1,6-diylbis[3-(3,5-di-tert-butyl-4-hydroxyphenylpropionamide)] (Irganox® 1098); pentaerythritol tetrakis[3-(3,5-di-tert-butyl-4-hydroxyphenyl)propionate] (Irganox® 1010); 2,6-di-tert-butyl-4-[4,6-bis(octylthio)-1,3,5-triazin-2-ylamino]phenol (Irganox® 565); 2-(2H-benzotriazole-2-yl)-4,6-bis(1-methyl-1-phenylethyl) phenol (Uvinul® 3034); trolamine salicylate (triethanolamine salicylate); diethylanolamine p-methoxycinnamate (DEA methoxycinnamate); polysilicone-15 (Parsol® SLX); CAS number 152261-33-1 (Uvinul® 5050H); 4-methylbenzylidene camphor (Eusolex® 6300, Parsol® 5000); bisoctrizole (Tinosorb® M); benzenamine, N-phenyl-, reaction products with 2,4,4-trimethylpentene (Irganox® 50507); sulisobenzone, Escalol®577); (2-ethylhexyl)-2-cyano-3,3-diphenylacrylate (Uvinul® 3039); digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-; bis-(2,2,6,6-tetramethyl-4-piperidyl)-sebacate (Uvinul® 4077H); benzophenone-5; 1,3,5-tris(3,5-di-tert-butyl-4-hydroxybenzyl)-1,3,5-triazine-2,4,6(1H,3H,5H)-trione (Irganox® 3114); hexamethylendiamine (Uvinul® 4050H); benzophenone-8 (dioxybenzone); ethyl-4-bis(hydroxypropyl)aminobenzoate (roxadimate); 6-tert-butyl-2-(5-chloro-2H-benzotriazole-2-yl)-4-methylphenol (Uvinul® 3026); p-aminobenzoic acid (PABA); 3,3',3'',5,5',5''-hexa-tert-butyl-α-α'-α''-(mesitylene-2,4,6-triyl)tri-p-cresol (Irganox® 1130); lawsone with dihydroxyacetone; benzophenone-9 (Uvinul® DS-49); benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor (Mexoryl® SD); terephthalylidene dicamphor sulfonic acid; camphor benzalkonium methosulfate (Mexoryl® SO); bisdisulizole disodium (Neo Heliopan® AP); etocrylene; ferulic acid; 2-(2H-benzotriazole-2-yl)-4-(1,1,3,3-tetramethylbutyl)-phenol (Uvinul® 3029); 4,6-bis(dodecylthiomethyl)-o-cresol (Irganox® 1726); beta-2-glucopyranoxy propyl hydroxy benzophenone; phenylbenzimidazole sulfonic acid (ensulizole, Eusolex® 232, Parsol® HS); benzophenone-3 (oxybenzone, Escalol® 567); diethylamine hydroxybenzoyl hexylbenzoate (Uvinul® A Plus); 3',3'-diphenylacryloyl)oxy]methyl}-propane (Uvinul® 3030); and ethylhexyl p-methoxycinnamate (Escalol® 557).

It is recognized that the suitability of UV absorbers in personal care compositions often depends on local regulatory laws; hence, the above list may include UV absorbers that are or are not allowed in certain regions.

In one embodiment, the sun care composition comprises one or more UV absorbers selected from the following: p-aminobenzoic acid (PABA), Padimate O, ensulizole, cinoxate, benzophenone-3, enzophenone-8, homosalate, meradimate, octocrylene, 2-ethylhexyl-p-methoxycinnamate, octyl salicylate, sulisobenzone, trolamine salicylate, avobenzone, ecamsule, titanium dioxide, zinc oxide, 4-methylbenzylidene, Tinosorb M, neo heliopan AP, mexoryl XL, benzophenone-9, Uvinul T150, Uvinul A Plus, Uvasorb HEB, Parsol SLX, and isopentenyl-4-methoxycinnamate.

Additionally, it will be recognized by one skilled in the art that tanning agents are sun care compositions, since they frequently contain one or more UV absorbers (typically at lower addition levels than found in sun blocks), along with moisturizers, emollients, and other adjuvants like fragrance.

Personal Care Compositions—Hair Care

The alcohol-solubility of the invented polymers also favors their formulation in hair care products, which frequently contain ethanol. These hair care products include rinse-off and leave-in products and are used to create a hair styling effect and/or benefit. Examples of the hair care products include shampoos, conditioners, hair sprays, mists, lotions, solutions, mousses, crèmes, gels, and serums. They may impart a reshapeable hair style, meaning they can be reshaped without the addition of new hair care material, or not impart a reshapeable hair style.

The composition according to the invention may be sprayable, for example by a pump, or may be a pressurized aerosol composition. It may be sprayable by a dispensing valve controlled by a dispensing head, which in turn comprises a nozzle, which vaporizes the aerosol composition. A sprayable composition according to the invention comprises an appropriate solvent. Advantageously, the appropriate solvent comprises at least one solvent chosen from water and lower molecular weight alcohols, such as ethanol.

When the sprayable composition according to the invention is an aerosol composition, it additionally comprises an appropriate amount of propellant. The propellant comprises compressed or liquefied hydrocarbon gases, which are normally employed for the preparation of aerosol compositions. Suitable gasses include compressed air, carbon dioxide, and nitrogen, which may be soluble in the composition, such as dimethyl ether, fluorinated or non-fluorinated hydrocarbons, and mixtures thereof.

The present invention additionally provides an aerosol device comprising a vessel comprising an aerosol composition, which comprises a liquid phase (or juice) comprising at least one sun care or hair styling material, as described above, in an appropriate medium and a propellant, and a dispenser, such as a dispensing valve, for dispensing said aerosol composition from the vessel.

The present invention additionally provides a method of treating keratinous fibers, especially hair, in which the composition according to the invention, as described above, is applied to the hair before, during, or after the shaping of the hairstyle.

The compositions according to the invention include those intended to be easily rinsed/washed off the hair, or exhibit varying degrees of waterfastness.

The invention additionally provides the use of a composition as described above in, or for the preparation of, a cosmetic reshapable hair styling formulation.

The determination of whether a composition with a (meth)acrylic copolymer according to the invention can provide a reshapable effect can be determined by an in vivo test.

Where the composition is in the form of a lotion, for example, the in vivo test proceeds as follows: The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cosmetic properties, and the reshapable effect. For example, once dried, the hair is brushed in different directions to remove the original styling. The hair is then brushed to restore the original styling. The process of removing the styling, restoring the styling, and evaluating the success of restoring the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10-20 different individuals.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

More generically, when the polymers are used in personal care compositions, the formula also can be formulated with other ingredients known to the cosmetic industry to give cosmetic compositions containing an aqueous component. Such ingredients include emollients, humectants, other film forming polymers, propellants, pigments, dyes, buffers, organic and inorganic suspending and thickening agents, waxes, surfactants and cosurfactants, plasticizers, preservatives, flavoring agents, perfumes, and active ingredients including sunscreen agents, insect repellents, vitamins, herbal extracts, antiperspirant and deodorant agents, skin or hair bleaching or coloring agents, depilating agents, antifungal and antimicrobial agents, antidandruff and antiacne agents, astringents, and corn, callus, and wart removers.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The compounds as well as polymers described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the polymers described herein find application in this art area may be found in the following publications by International Specialty Products: Health and nutrition product guide—Performance enhancing products (August 2008), Plasdone® povidones product overview (April 2010), Plasdone® K-12 and K-17 providones—Solubilizers for liquid softgel fill formulations (September 2010), Plasdone® K-29/32 povidone—High efficiency binder for wet granulation (April 2010), Plasdone® S-630 copovidone—Product Overview (April 2010), Polyplasdone® Ultra and Ultra-10 crospovidones—Product overview (September 2010), Polyplasdone® superdisintegrants—Product overview (July 2010), Polyplasdone® crospovidone—Superdisintegrants for orally disintegrating and chewable tablets (July 2010), Polyplasdone® crospovidone—Nonionic superdisintegrant for improved dissolution of cationic drugs (July 2009), Polyplasdone® crospovidone—The solution for poorly soluble drugs (July 2009), Polyplasdone® crospovidone—Novel pelletization aid for extrusion spheronization (July 2010), PVP-Iodine povidone iodine antiseptic agent (March 2004), and Pharmaceutical technical bulletin—PVP-Iodine for prophylaxis and treatment of bovine mastitis (December 2003). Each publication is hereby incorporated in its entirety by reference.

Any range in composition pH may be used. In embodiments wherein the composition is applied to keratinous material, the pH may range from about 2 to 12. pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, $\alpha$-hydroxyacids, $\beta$-hydroxyacids, $\alpha,\beta$-hydroxyacids, $\alpha$-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine(2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

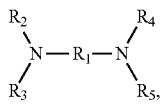

wherein $R_1$ is a propylene residue that may be optionally substituted with an hydroxyl group or a C1-C4 alkyl radical; $R_2$, $R_3$, $R_4$ and $R_5$ are identical or different and represent a hydrogen atom, a C1-C4 alkyl radical or C1-C4 hydroxyalkyl radical.

The composition also may comprise one or more buffers. Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate. The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions of the invention may also take the form of skin-washing compositions, and particularly in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, homemanicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077; 970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by International Specialty Products, each of which is hereby incorporated in its entirety by reference: Plasdone® K-29/32, Advanced non-oxidative, non-abrasive teeth whitening in toothpastes, mouthwashes, and oral rinses (2010), Polymers for oral care, product and applications guide (2002), A formulation guide for excellent hair styling gels and lotions (April 2003), PVP (polyvinylpyrrolidone) (no date provided), and Textile chemicals, solutions for the most challenging product environment (no date provided).

Also contemplated are additional personal care compositions that may comprise the polymers described herein. Disclosures on such compositions may be found in the publications listed below, each of which is hereby incorporated in its entirety be reference: (1) Prototype Formulations—Personal Care Products (2009) from Xiameter, Dow Corning. (2) Sun care formulations under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorhydrates, aluminium zirconium chlorhydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin lighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip-.com, the contents of each of these disclosures are hereby incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are hereby incorporated in their entirety by reference.

Any known conditioning agent may be used in the personal care compositions of the invention. An extensive discussion on conditioning agents may be found in the book Conditioning Agents for Skin and Hair, Cosmetic Science and Technology Series, Volume 21, 1999, Marcel Dekker Publishers. The contents of the book is hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, litsea cubeba, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or micro-emulsions.

The cationic polymers that may be used as conditioning agents according to the invention generally have a molecular weight (average number) from about 500 Da to about 5,000,000 Da, and particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat® by International Specialty Products; terpolymers of dimethyl amino ethyl methacrylate, vinyl caprolactam, and vinyl pyrrolidone such as the product sold under the name Gaffix® VC 713 by International Specialty Products; the vinyl pyrrolidone/methacrylamidopropyl dimethylamine copolymer, marketed under the name Styleze® CC 10 by International Specialty Products; and the vinyl pyrrolidone/quaternized dimethyl amino propyl methacrylamide copolymers such as the product sold under the name Gafquat® HS 100 by International Specialty Products (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a C12 alkyl group, Croquat® M, in which the quaternary ammonium groups include C10-C18 alkyl groups, Croquat® S in which the quaternary ammonium groups include a C18 alkyl group, Crotein® Q in which the quaternary ammonium groups include at least one C1-C18 alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N-(2-hydroxy ethyl)-N-(3-cetoxyl-2-hydroxy propyl)amide of cetylic acid, N-docosanoyl N-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), N-Hance™ SP-100 (INCI Name: acrylamidopropyl trimonium chloride/acrylamide copolymer), and N-Hance™ cationic guar (INCI Name: guar hydroxypropyltrimonium chloride) from Ashland Inc.

(2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze® 7 and Conditioneze® NT-20 from International Specialty Products (Wayne, N.J.).

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bis-biquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethyl-stearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In particular embodiments, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In particular embodiments, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

In one of the embodiment, the compositions of the invention may be anhydrous.

Typically, sun care compositions may also comprise one or more UV actives, which include organic and inorganic materials that scatter, absorb, and/or reflect radiation having a wavelength from about 100 nm to about 400 nm.

In one particular embodiment, the sun care compositions protect against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm.

In another embodiment, the sun care compositions may not contain UV actives, and may be regarded as tanning oils or tan promoters.

Sun care compositions may be formulated, for example, for application to the lips, hair, face, cheeks, neck, area around the eyes, full hands, and body area. Self-tanning compositions, which are products that color skin without requiring full sun exposure, also fit under the sun care umbrella.

Suitable UV absorber(s) that may be included in the personal care compositions most likely will depend on local regulations. As the rules governing the names and usage levels evolve over time, it is impossible to include every UV absorber that may be used with the invention.

Non-limiting examples of suitable UV absorbers include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomenthyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3'',5,5',5''-hexa-tert-butyl-α-α'-α''-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Personal care compositions may comprise antioxidant(s) and/or antiradical protecting agent(s).

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled Minerals for Personal Care from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from The Lubrizol Corporation.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; astragalus gummifer gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; *caesalpinia spinosa* gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; *ceratonia siliqua* gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; *glycine soja* (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; iso stearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; *sclerotium* gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; *sterculia urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, N-Hance™ cationic guar, N-Hance™ HP Series hydroxypropyl guar, N-Hance™ SP-100 conditioning polymer, and Supercol™ guar gum from Ashland Inc.

(2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze®, Rapithix® A-60, Rapithix® A-100, Ultrathix® P-100, Lubrajel® and FlexiThix from International Specialty Products (Wayne, N.J.).

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in Chemistry and Biology; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice formulations are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting polymerized resins as described in U.S. Pat. No. 3,070,510.

Non-limiting examples of suitable resins include: melamines, phenolics, ureas, melamine-ureas, melamine-formaldehydes, urea-formaldehyde, melamine-urea-formaldehydes, cross-linked epoxides, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. No. 3,538,230, and U.S. Pat. No. 3,862,307.

Non-limiting examples of suitable silica abrasives include: silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate)poly(amide), poly(ethylene amine), poly(ethylene glycol), poly(propylene glycol), poly(vinyl acetate), poly(vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®), as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the present compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in Kirk-Othmer Encyclopedia of Chemical Technology, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, carbamide peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition. A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O_6)_a(C_2H_4O)_bH$ wherein a is an integer such that the hydrophobic base represented by $(C_3H_6O_6)$ has a molecular weight of about 2,750 Da to 4000 Da, b is an integer such that the hydrophilic portion (moiety) represented by $(C_2H_4O)$ constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s).

Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as *thaumatoccous danielli* (Thaumatin I and II) may be used. The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include *capsicum* and nicotinate esters such as benzyl nicotinate. Non-limiting examples of suitable numbing agents include benzocaine, lidocaine, clove bud oil, ethanol, and blends thereof.

Oral care compositions may comprise chelating agent(s). The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethylidene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose or "CMC") and long-acting polymers (e.g., poly[vinyl methyl ether maleate], or "Gantrez" and its salts). Polyvinylpyrrolidone (povidone) may also be used.

Other components of denture adhesive products impart particular physical attributes to the formulations. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

Performance Chemicals Compositions

The invention's polymers also may be employed in any number of various performance chemicals compositions. Examples of performance chemicals compositions include: adhesives, coatings, electronics, inks, paper, paints, polish, printing, plasters, and wood-care compositions.

Polymers of the invention also may be used as an adhesive, adhesive promoter, antennae for radio-frequency identification (RFID), binder (for wood, rubber, recycled materials, flooring, carpet underlays, moulding for steel casting), circuit board fabrication, coatings (e.g., for steel, concrete, wood, cellulose materials, release coatings), fabric softening, foam (bedding, car seats, filling material, furniture, headrests, mattresses, pillows, transportation cabin components), elastomers (e.g., rollers, belts, roller blades, printing rollers, hoses), insulation (residential, commercial, institutional constructions), medical and diagnostic devices/instrumentation/sensors, microelectronic devices (e.g., for environmental, mechanical, and dampening protection, and sensors and optoelectronics), rigid insulating foam, sealants, underfill encapsulants, and water repellency (e.g., glass, leather, paper, fabric surfaces, powders).

Furthermore, the alcohol-soluble polymers described herein also may be formulated as coatings and polishes. These compositions can be presented as aqueous dispersions or hydroalcoholic solutions, with a concentration of solids typically from about 10%-70% (w/w), or more preferably in the range of about 10%-60% (w/w). The incorporation of the lower molecular weight alcohol(s) into the formulation (since the invention's polymers are themselves alcohol soluble), may be exploited to accomplish fast-drying coatings and polishes.

Polymers of the invention also may be used to create an optical, laminated film, obtained by laminating an adhesive layer having the described adhesive (which has the inventive polymer) on both surfaces or one surface of an optical film. This film is one any an optical property, such as a polarizing film, phase retardation film, and other examples are known to those skilled in the art.

The optical films also may have a protective film that is further applied. Examples of the protective film include films composed of acrylic resins different from the acrylic resin of the present invention, acetylcellulose-based films such as a cellulose triacetate film and the like, polyester resin films, olefin resin films, polycarbonate resin films, polyether ketone resin films, polysulfone resin films and the like. In the protective film, ultraviolet absorbers such as a salicylate-based compound, benzophenone-based compound, benzotriazole-based compound, triazine-based compound, cyanoacrylate-based compound, nickel complex salt-based compound and the like may be compounded. In the protective films, acetylcellulosed-based films are suitably used.

Another use of the polymers is in coatings and polishes that are not tacky or sticky, given the polymer's high glass transition temperatures. These coatings may be used for flooring, furniture, walls, and other similar surfaces, and be transparent, semi-transparent, or opaque in appearance. Particular are transparent and semi-transparent coatings and polishes. Coatings and polishes having the polymers described herein may be used to impart gloss/shine, endurance, water resistance, and/or washability.

It is anticipated that such coatings and polishes will contain other ingredients, such as plasticizers, other film-formation agents, wettability agents, pH adjusters, and/or other polymers. If colored or opaque coatings and polishes are desired, then customary dyes or pigments may be added. Coatings and polishes may take the form of a concentration for subsequent dilution, as a ready-made solution/dispersion, a paste, wax, wipe, spray, or mist. To achieve these product formats customary co-ingredients may be necessary, such as an aerosol propellant or viscosifier.

EXAMPLES

Example 1

Synthesis of poly(21.1% VP-32.5% AA-41.2% IBMA-5.3% IBOMA)

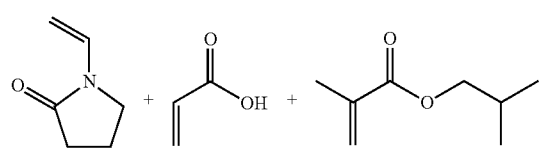

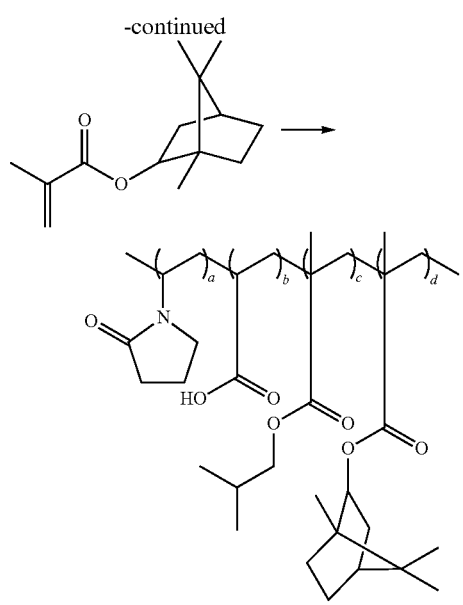

An autoclave reactor was loaded with a solution of N-vinyl-2-pyrrolidone (13.33 g), acrylic acid (13.33 g), isobutyl methacrylate (33.33 g), and isobornyl methacrylate (6.67 g) in ethanol (68.00 g). The mixture was heated to 80° C. under nitrogen with mechanical stifling at 200 rpm. At this time a pump was filled with a mixture of N-vinyl-2-pyrrolidone (26.67 g), acrylic acid (26.67 g), isobutyl methacrylate (66.67 g), and isobornyl methacrylate (13.33 g). At t=0, t-amyl peroxy-2-ethylhexanoate initiator (Trigonox 121, Akzo Nobel) (0.30 g) was charged into the reactor to initiate the polymerization. Then, the contents of the pump were emptied into the reactor at a constant rate over the next 3 hours. Additional shots of the initiator were added at t=1, 2, 3 hour (0.30 g each). The reaction temperature was then raised to 91° C. at t=5 hour and additional initiator was charged at t=5 and 8 hours (0.60 g each). After the last initiator addition, the reactor was kept stifling at 91° C. for 4 hours. After cooling, a clear viscous copolymer solution was discharged into a glass bottle. The polymer was then isolated by standard separation means into dry powder form.

Examples 2-5

Synthesis of Other poly(VP-AA-IBMA-IBOMA) Polymers

The method of Example 1 was substantially repeated to yield other non-homopolymers of differing monomer ratios (Table 1). All polymers were soluble in ethanol at 50% solids (w/w).

TABLE 1

Poly(VP-AA-IBMA-IBOMA) polymers

| Ex. | monomer content (mole percent) | | | | monomer content (weight percent) | | | |
|---|---|---|---|---|---|---|---|---|
| | VP | AA | IBMA | IBOMA | VP | AA | IBMA | IBOMA |
| 1 | 10.8 | 33.3 | 50.6 | 5.4 | 10 | 20 | 60 | 10 |
| 2 | 11.1 | 34.3 | 43.5 | 11.11 | 10 | 20 | 50 | 20 |
| 3 | 16.2 | 33.4 | 42.3 | 8.1 | 15 | 20 | 50 | 15 |

TABLE 1-continued

Poly(VP-AA-IBMA-IBOMA) polymers

| | monomer content (mole percent) | | | | monomer content (weight percent) | | | |
|---|---|---|---|---|---|---|---|---|
| Ex. | VP | AA | IBMA | IBOMA | VP | AA | IBMA | IBOMA |
| 4 | 21.1 | 32.5 | 41.2 | 5.3 | 20 | 20 | 50 | 10 |
| 5 | 21.1 | 32.5 | 41.2 | 5.3 | 20 | 20 | 50 | 10 |

Examples 6-8

Synthesis of poly(VCL-AA-IBMA-IBOMA) Non-Homopolymers

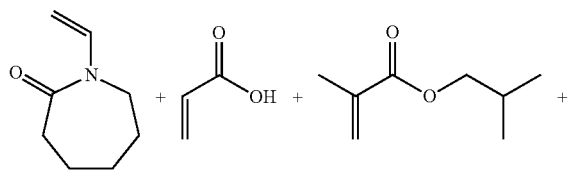

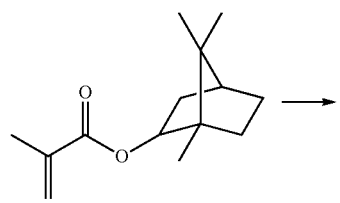

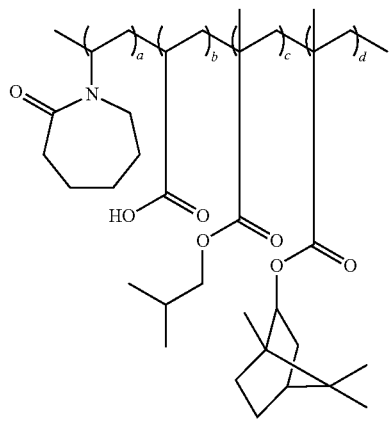

Examples 3, 4, and 5 were substantially repeated, replacing VP by an equal amount of N-vinyl-2-caprolactam (VCL) on a weight basis (Table 2). As in Examples 2-5, the polymers of Examples 6 and 7 were made in ethanol and were soluble in the final product at 50% solids (w/w). The non-homopolymer of Example 8 was synthesized in acetone, and created a cloudy product mixture.

TABLE 2

Poly(VCL-AA-IBMA-IBOMA) polymers

| | monomer content (mole percent) | | | | monomer content (weight percent) | | | |
|---|---|---|---|---|---|---|---|---|
| Ex. | VCL | AA | IBMA | IBOMA | VCL | AA | IBMA | IBOMA |
| 6 | 13.4 | 34.5 | 43.7 | 8.4 | 15 | 20 | 50 | 15 |
| 7 | 17.6 | 33.9 | 43.0 | 5.5 | 20 | 20 | 50 | 10 |
| 8 | 17.6 | 33.9 | 43.0 | 5.5 | 20 | 20 | 50 | 10 |

Example 9

Relative Viscosity of Polymers

The relative viscosities (RV) of the polymers of Examples 1-5 were measured at 1% (w/v) concentration in ethanol at 25° C. RVs of the poly(VP-AA-IBMA-IBOMA) polymers ranged from 1.31-1.36 (Table 3).

TABLE 3

Measured RVs of ethanol-soluble poly(VP-AA-IBMA-IBOMA) polymers

| polymer of Example | RV |
|---|---|
| 1 | 1.36 |
| 2 | 1.32 |
| 3 | 1.34 |
| 4 | 1.31 |
| 5 | 1.33 |

Example 10

Thermal Properties of Ethanol-Soluble Polymers

The glass transition temperatures ($T_g$) and decomposition temperatures (DT) were measured for polymers from Examples 1-5. The reported $T_g$ was obtained using a heating rate of 20° C./min from the second heating cycle after first heating the sample from 25° C. to 250° C. Fresh samples were used to measure the DT by heating them from 25° C. to 600° C. at 20° C./min.

Every polymer had a $T_g$ greater than 100° C. Polymers from Examples 2-4 had $T_g$ greater than 110° C. (Table 4). Thus, polymers of the invention are not tacky nor sticky at ambient temperatures (about 20° C.-25° C.), which, in part, suggests their use in various applications. Furthermore, every polymer had a DT greater than 330° C., suggesting their use in many non-cosmetic compositions.

TABLE 4

Thermal properties of ethanol-soluble polymers

| polymer of Example | $T_g$ (° C.) | DT (° C.) |
|---|---|---|
| 1 | 106 | 343 |
| 2 | 118 | 334 |
| 3 | 113 | 333 |
| 4 | 113 | 348 |

Examples 11A-11E

Sun Care Formulations Having poly(VP-AA-IBMA-IBOMA)

The polymers of Examples 1-5 were formulated in the sun care formulas (Table 5) to evaluate their effectiveness in boosting UV radiation absorption. A comparative example also were prepared that did not contain any polymer additive (balance added to ethanol).

All five polymers of the invention boosted UV absorption 50%-70% compared to control 1 that was lacking the non-homopolymer of the invention (FIGURE).

TABLE 5

Sun care formulation tested in Example 11.

| example | ingredients | addition level (% w/w) | supplier |
|---|---|---|---|
| 11A-11E | polymer from Example 1, 2, 3, 4, or 5 | 1.0 | |
| | avobenzone (Escalol ® 517) | 3.0 | ASI |
| | oxybenzone (Escalol ® 567) | 5.0 | ASI |
| | homosalate (Eusolex HMS) | 10.0 | EMD |
| | octisalate (Escalol ® 587) | 5.0 | ASI |
| | octocrylene (Escalol ® 597) | 10.0 | ASI |
| | ethanol | 66.0 | |
| | total | 100.0 | |

Comparative Example 1

Synthesis of poly(1.4% VP-2.1% AA-84.4% IBMA-12.1% IBOMA) (Mole Fractions)

The method of Example 1 was followed, except that the kettle reactor was initially charged with 68 g of ethanol, 0.67 g of N-vinyl-2-pyrrolidone, 0.67 g of acrylic acid, 53.33 g of isobutyl methacrylate, and 12.00 g of isobornyl methacrylate and that the monomer feeding was composed of 1.33 g of N-vinyl-2-pyrrolidone, 1.33 g of acrylic acid, 106.67 g of isobutyl methacrylate, and 24.00 g of isobornyl methacrylate. After cooling, a viscous polymer solution was discharged into a glass bottle.

Solubility tests showed this polymer had a solubility of less than 1% solids (w/w) in ethanol at 25° C.

What we claim is:

1. A non-crosslinked non-homopolymer comprising:
(A) 10-22 mole percent of at least one N-vinyl lactam,
(B) 30-35 mole percent of at least one monomer selected from the group consisting of acrylic acid (AA), methacrylic acid, and combinations thereof,
(C) 40-52 mole percent of at least one (meth)acrylate of a straight- or branched- chain alkyl alcohol, and
(D) 5-20 mole percent of at least one (meth)acrylate of a saturated or unsaturated cyclic or bicyclic alcohol having 6 to 20 carbon atoms,
wherein said non-homopolymer has a glass transition temperature of at least 100° C., and has at least 1% (w/w) solubility at 25° C. in at least one alcohol selected from the group consisting of: ethanol, 1-propanol, 2-propanol, methanol, and combinations thereof.

2. The non-homopolymer according to claim 1 wherein said N-vinyl lactam is selected from the group consisting of: N-vinyl-2-pyrrolidone (VP), N-vinyl-2-piperidone, N-vinyl-2-caprolactam (VCL), and combinations thereof.

3. The non-homopolymer according to claim 1 wherein said (meth)acrylate of straight- or branched-chain alkyl alcohol is selected from the group consisting of: isobutyl acrylate, isobutyl methacrylate (IBMA), tert-butyl acrylate, tert-butyl methacrylate, and combinations thereof.

4. The non-homopolymer according to claim 1 wherein said (meth)acrylate of a saturated or unsaturated cyclic or bicyclic alcohol is selected from the group consisting of: isobornyl acrylate, isobornyl methacrylate (IBOMA), and combinations thereof.

5. The non-homopolymer of claim 1 comprising:
(A) 10-22 mole percent of an N-vinyl lactam selected from the group consisting of N-vinyl-2-pyrrolidone (VP), N-vinyl-2-caprolactam (VCL), and combinations thereof,
(B) 30-35 mole percent acrylic acid (AA),
(C) 40-52 mole percent isobutyl methacrylate (IBMA), and
(D) 5-20 mole percent isobornyl methacrylate (IBOMA).

6. The non-homopolymer according to claim 5 that is essentially:
poly (11% N-vinyl-2-pyrrolidone (VP)-33% acrylic acid (AA)-51% isobutyl methacrylate (IBMA)-5% isobornyl methacrylate (IBOMA)),
poly (11% N-vinyl-2-pyrrolidone (VP)-34% acrylic acid (AA)-44% isobutyl methacrylate (IBMA)-11% isobornyl methacrylate (IBOMA)),
poly (16% N-vinyl-2-pyrrolidone (VP)-34% acrylic acid (AA)-42% isobutyl methacrylate (IBMA)-8% isobornyl methacrylate (IBOMA)),
poly (21% N-vinyl-2-pyrrolidone (VP)-33% acrylic acid (AA)-41% isobutyl methacrylate (IBMA)-5% isobornyl methacrylate (IBOMA)),
poly (13% N-vinyl-2-caprolactam (VCL)-35% acrylic acid (AA)-44% isobutyl methacrylate (IBMA)-8% isobornyl methacrylate (IBOMA)), or
poly (17% N-vinyl-2-caprolactam (VCL)-34% acrylic acid (AA)-43% isobutyl methacrylate (IBMA)-6% isobornyl methacrylate (IBOMA)),
wherein all percentages are mole percent.

7. The non-homopolymer according to claim 1, wherein said non-homopolymer is at least 50% (w/w) soluble at 25° C. in at least one alcohol selected from the group consisting of: ethanol, 1-propanol, 2-propanol, methanol, and combinations thereof.

8. A personal care composition comprising a non-crosslinked non-homopolymer comprising:
(A) 10-22 mole percent of at least one N-vinyl lactam,
(B) 30-35 mole percent of at least one monomer selected from the group consisting of acrylic acid (AA), methacrylic acid, and combinations thereof,
(C) 40-52 mole percent of at least one (meth)acrylate of a straight- or branchedchain alkyl alcohol, and
(D) 5-20 mole percent of at least one (meth)acrylate of a saturated or unsaturated cyclic or bicyclic alcohol having 6 to 20 carbon atoms,
wherein said non-homopolymer has a glass transition temperature of at least 100° C., and has at least 1% (w/w) solubility at 25° C. in at least one alcohol selected from the group consisting of: ethanol, 1-propanol, 2-propanol, methanol, and combinations thereof.

9. The personal care composition according to claim 8 wherein said non-homopolymer comprises:
(A) 10-22 mole percent of an N-vinyl lactam selected from the group consisting of N-vinyl-2-pyrrolidone (VP), N-vinyl-2-caprolactam (VCL), and combinations thereof, (B) 30-35 mole percent acrylic acid (AA),
(C) 40-52 mole percent isobutyl methacrylate (IBMA), and
(D) 5-20 mole percent isobornyl methacrylate (IBOMA),
wherein said non-homopolymer has a glass transition temperature of at least 100° C., and has at least 1% (w/w) solubility at 25° C. in at least one alcohol selected from the group consisting of ethanol, 1-propanol, 2-propanol, methanol, and combinations thereof.

10. The personal care composition according to claim 8 that is a skin lotion, skin creme, skin ointment, skin salve, anti-aging creme, moisturizer, deodorant, tanning agent, sun block, foundation, concealer, eyebrow pencil, eye shadow, eye liner, mascara, rouge, finishing powder, lipstick, lip gloss, nail polish, make-up remover, nail polish remover, shampoo, rinse-off conditioner, leave-on conditioner, hair styling gel, hair mousse, hair spray, styling aide, hair color, or hair color remover.

11. The personal care composition according to claim 10 that comprises one or more UV absorbers selected from the group consisting of: p-aminobenzoic acid (PABA), octyl dimethyl PABA, phenylbenzimidazole sulfonic acid, benzophenone-3, Q enzophenone-8, homomenthyl salicylate, menthyl anthranilate, octocrylene, 2-ethylhexyl-p-methoxycinnamate, octyl salicylate, sulisobenzone, trolamine salicylate, avobenzone, ecamsule, titanium dioxide, zinc oxide, 4-methylbenzylidene, bisoctrizole, bisdisulizole disodium, drometrizole trisiloxane, benzophenone-9, ethylhexyl triazone, diethylamino hydroxybenzoyl hexyl benzoate, iscotrizinol, polysilicone-15, isopentenyl-4-methoxycinnamate, and combinations thereof.

12. A method of boosting UV absorbance comprising the step: formulating a composition comprising at least one UV absorber and at least one non-crosslinked non-homopolymer comprising:
(A) 10-22 mole percent of at least one N-vinyl lactam,
(B) 30-35 mole percent of at least one monomer selected from the group consisting of acrylic acid (AA), methacrylic acid, and combination thereof,
(C) 40-52 mole percent of at least one (meth)acrylate of a straight- or branched chain alkyl alcohol, and
(D) 5-20 mole percent of at least one (meth)acrylate of a saturated or unsaturated cyclic or bicyclic alcohol having 6 to 20 carbon atoms,
wherein said non-homopolymer has a glass transition temperature of at least 100° C., and has at least 1% (w/w) solubility at 25° C. in at least one alcohol selected from the group consisting of ethanol, 1-propanol, 2-propanol, methanol, and combinations thereof.

13. The method according to claim 12 wherein said non-homopolymer comprising:
A) 10-22 mole percent of an N-vinyl lactam selected from the group consisting of N-vinyl-2-pyrrolidone (VP), N-vinyl-2-caprolactam (VCL), and combinations thereof,
(B) 30-35 mole percent acrylic acid (AA),
(C) 40-52 mole percent isobutyl methacrylate (IBMA), and
(D) 5-20 mole percent isobornyl methacrylate (IBOMA).

14. The method according to claim 12 that increases UV absorbance by about 50% or more compared to a similarly formulated composition lacking said nonhomopolymer.

15. The method according to claim 12 wherein said UV absorber is selected from the group consisting of: p-aminobenzoic acid (PABA), octyl dimethyl PABA, phenylbenzimidazole sulfonic acid, benzophenone-3, benzophenone-8, homomenthyl salicylate, menthyl anthranilate, octocrylene, 2-ethylhexyl-p-methoxycinnamate, octyl salicylate, sulisobenzone, trolamine salicylate, avobenzone, ecamsule, titanium dioxide, zinc oxide, 4-methylbenzylidene, bisoctrizole, bisdisulizole disodium drometrizole trisiloxane, benzophenone-9, ethylhexyl triazone diethylamino hydroxybenzoyl hexyl benzoate iscotrizinol polysilicone-15 isopentenyl-4-methoxycinnamate, and combinations thereof.

16. A performance chemicals composition comprising a non-crosslinked non-homopolymer derived comprising:
(A) 10-22 mole percent of at least one N-vinyl lactam,
(B) 30-35 mole percent of at least one monomer selected from the group consisting of acrylic acid (AA), methacrylic acid, and combinations thereof,
(C) 40-52 mole percent of at least one (meth)acrylate of a straight- or branched chain alkyl alcohol, and
(D) 5-20 mole percent of at least one (meth)acrylate of a saturated or unsaturated cyclic or bicyclic alcohol having 6 to 20 carbon atoms,
wherein said non-homopolymer has a glass transition temperature of at least 100° C., and has at least 1% (w/w) solubility at 25° C. in at least one alcohol selected from the group consisting of ethanol, 1-propanol, 2-propanol, methanol, and combinations thereof.

17. The performance chemicals composition according to claim 16 wherein said non-homopolymer comprises:
(A) 10-22 mole percent of an N-vinyl lactam selected from the group consisting of N-vinyl-2-pyrrolidone (VP), N-vinyl-2-caprolactam (VCL), and combinations thereof,
(B) 30-35 mole percent acrylic acid (AA),
(C) 40-52 mole percent isobutyl methacrylate (IBMA), and
(D) 5-20 mole percent isobornyl methacrylate (IBOMA),
wherein said non-homopolymer has a glass transition temperature of at least 100° C., and has at least 1% (w/w) solubility at 25° C. in at least one alcohol selected from the group consisting of ethanol, 1-propanol, 2-propanol, methanol, and combinations thereof.

18. The performance chemicals composition according to claim 17 that is an adhesive, coating, electronic, ink, paper, paint, polish, printing, plaster, energy, oilfield, or wood-care composition.

* * * * *